United States Patent [19]
Owens

[11] 4,205,670
[45] Jun. 3, 1980

[54] CHILD'S RESTRAINING HARNESS

[76] Inventor: James R. Owens, 18107 Central Ave., Upper Marlboro, Md. 20870

[21] Appl. No.: 963,726

[22] Filed: Nov. 27, 1978

[51] Int. Cl.² .......................................... A61F 13/00
[52] U.S. Cl. ..................................................... 128/134
[58] Field of Search ............... 128/133, 134; 297/473, 297/483, 487, 488, 385, 389; 244/122

[56] References Cited

U.S. PATENT DOCUMENTS

| | | | |
|---|---|---|---|
| 1,407,408 | 2/1922 | Gray | 297/487 |
| 2,288,692 | 7/1942 | Fearson | 297/473 |
| 2,633,906 | 4/1953 | Franz | 297/488 |
| 3,301,594 | 1/1967 | Pukish | 297/473 |
| 3,321,247 | 5/1967 | Dillender | 297/473 |
| 3,385,633 | 5/1968 | Aizley | 297/473 |
| 3,512,830 | 5/1970 | Norman et al. | 297/484 |
| 3,529,864 | 9/1970 | Rose et al. | 297/473 |
| 3,834,758 | 9/1974 | Soule | 297/389 |

FOREIGN PATENT DOCUMENTS

| | | | |
|---|---|---|---|
| 207664 | 1/1957 | Australia | 297/473 |
| 2242744 | 3/1974 | Fed. Rep. of Germany | 297/486 |

*Primary Examiner*—Lawrence W. Trapp
*Attorney, Agent, or Firm*—Schwartz, Jeffery, Schwaab, Mack, Blumenthal & Koch

[57] ABSTRACT

The present invention comprises a restraining harness for use on school buses, vans and other vehicles having a pair of straps and means for removably interconnecting the ends of the straps around the seat back for securingly attaching the harness to the seat back. A plurality of generally parallel, aligned loops are formed on each strap with a waist belt and a chest belt extending through respective pairs of generally aligned loops. The ends of the belts are connected together by means of material including minute hook members and pile or loop members on the other of the belt end.

7 Claims, 4 Drawing Figures

CHILD'S RESTRAINING HARNESS

FIELD OF THE INVENTION

The invention relates to a harness for use by handicapped children, particularly retarded children, in restraining the child in a school bus, van or like seat.

BACKGROUND OF THE INVENTION

One type of restraining harness used for restraining children includes a jacket-type arrangement wherein the child must be put into the jacket, and the jacket includes fastening means connected to the seat or the bus in a permanent manner as by anchoring straps to the floor of the school bus. This type arrangement is costly to use and requires that one size jacket be used in winter when the child wears a coat and another in summer when the child wears no coat.

Australian Pat. No. 255,971 illustrates a safety belt and harness which also includes means for securing a strap to the seat and has hook and loop type fastening means for a belt which may be positioned in one of two locations. This enables the belt to be secured around the waist or chest of the user; however, it does not permit chest and waist use, and more importantly, it does not permit a wide range of adjustable locations necessary in dealing with children of various sizes and ages.

Canadian Pat. No. 447,355 has means for restraining a child in a car seat, including a waist belt which is adjustably clipped to a pair of U-shaped wire clamps positioned over the top of a car seat. The flexibility and intention of the device is somewhat different than the instant invention.

Other prior art harnesses and restraints are illustrated in U.S. Pat. Nos. 1,048,033; 2,572,149; 2,739,642; 2,833,343 and 3,992,057. Each of these devices shows harnesses or restrainers designed for specific purposes, but none has the flexibility and adjustability of the instant invention.

OBJECTS OF THE INVENTION

It is an object of the instant invention to provide an economical and adjustable harness for use by children, particularly on school buses, vans and the like.

Another object is to provide a harness which includes both waist and chest restraints and is adjustable both as to the height of the child and the chest and waist size of the child.

Another object is to provide a harness for use on school buses which need not be permanently attached to the bus and which has a number of interchangeable straps and belts, wherein one portion can be replaced without replacing the entire unit.

SUMMARY OF THE INVENTION

The present invention comprises a restraining harness for use on school buses, vans and other vehicles having a pair of straps and means for removably interconnecting the ends of the straps around the seat back for securingly attaching the harness to the seat back. A plurality of generally parallel, aligned loops are formed on each strap with a waist belt and a chest belt extending through respective pairs of generally aligned loops. The ends of the belts are connected together by means of material including minute hook members and pile or loop members on the other of the belt end.

BRIEF DESCRIPTION OF THE DRAWINGS

The above and other objects of the invention will be apparent from the following description taken in conjunction with the accompanying drawings, wherein.

DETAILED DESCRIPTION OF THE INVENTION

Figure 4:
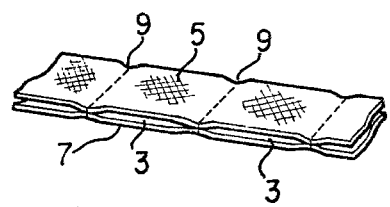
FIG. 4 is a perspective view of a portion of the harness.

A pair of straps 1 include a plurality of slotted openings 3 seen in detail in FIG. 4. The openings 3, shown as ten in number on each strap, are formed by a top portion 5 and a bottom portion 7 sewn together by stitching 9.

The straps 1 can either be two layers of, for example, seat belt webbing joined by additional stitching or preferably by an overlay stitched together by bottom stitching 11 and top stitching 13 with the above mentioned intermediate stitching 9. A pair of D-ring loops 15 are connected to one end of each of the straps 1. Selectively inserted in slots 3 are a pair of substantially parallel, horizontal restraining members in the form of a waist restraint 17 and a chest restraint 19. Restraints 17 and 19 include a hook-loop or hook-pile fastener arrangement including hooks 21 and loop-type means or pile 23 and are preferably of material sold under the trademark "VELCRO".

Figure 1:
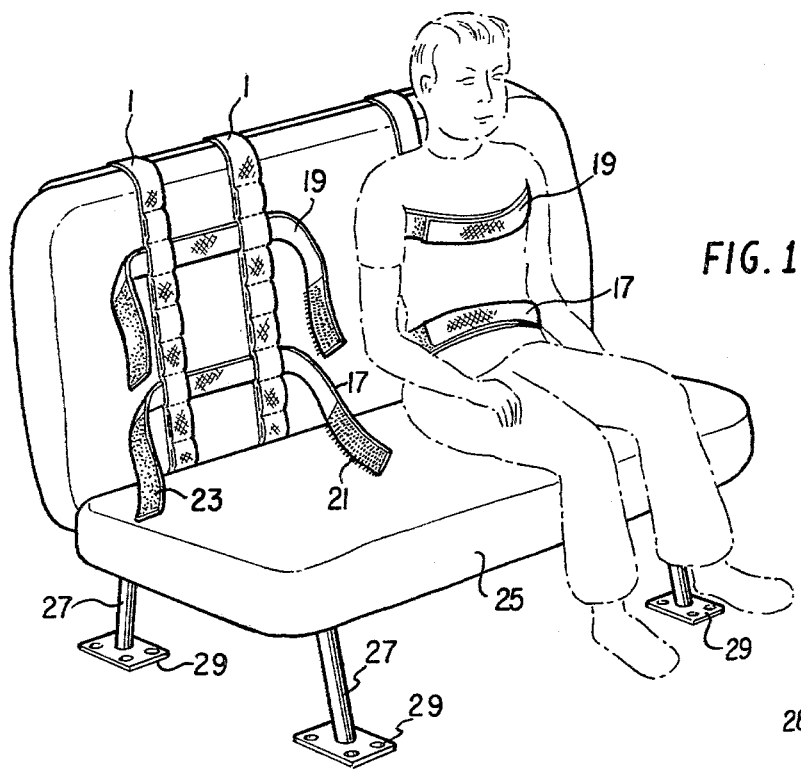
FIG. 1 is a perspective view of the invention seen attached to a bench-type school bus seat, and with an occupant strapped therein.
Figure 3:
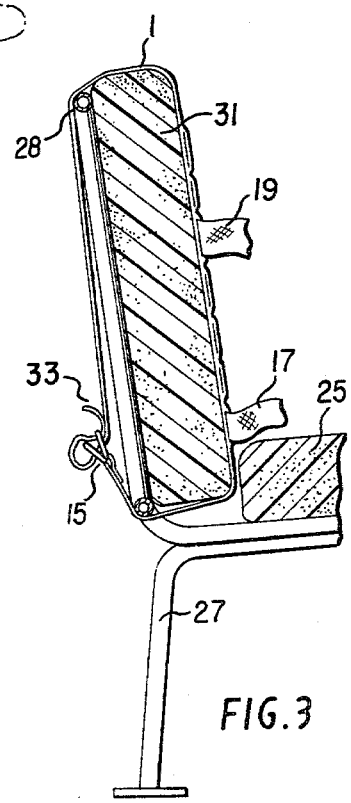
FIG. 3 is a side elevation view of the seat of FIG. 1 partially in cross section showing the harness attached to the seat.
Figure 2:
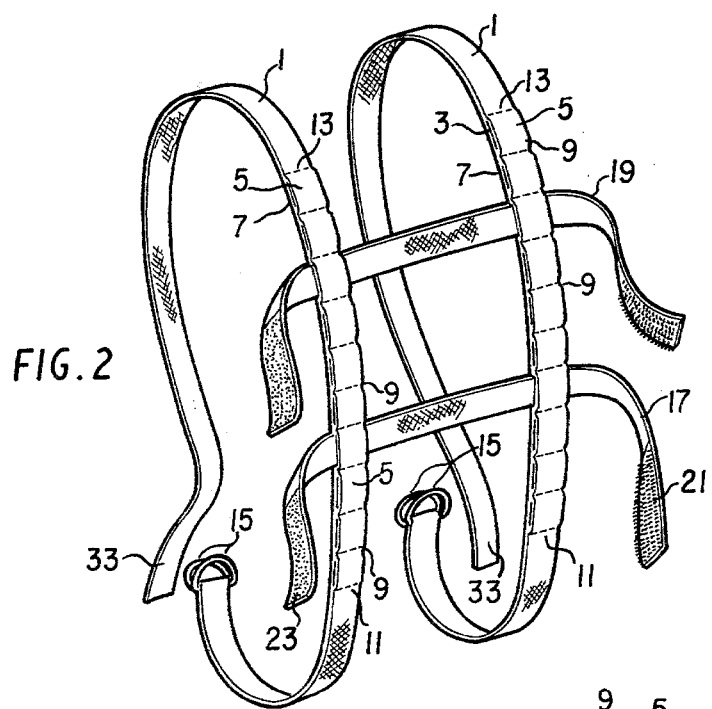
FIG. 2 is a perspective view of the invention in its disassembled position.

The unit is attached to a school bus or other bench-type seat as seen in FIGS. 1 and 3, the seat including a bench seat member 25 secured to the floor by means of legs 27 and attaching bracket means 29. The seat further includes a back member 31 attached by means of back tubing 29 and other support means. The harness is attached to the seat by passing the strap members 1 between seat member 25 and back 31 as best seen in FIG. 4. A free end of the belt 33 is inserted through the D-rings 15, over the top of the lower D-ring and through the upper D-ring as, again, illustrated in FIG. 3. In this manner, the harness can be securely attached to the seat. If desired, other fastening means such as material 21, 23 or buckles could be used in place of rings 15. The straps are easily removable by an adult; however, they are more difficult to remove for a handicapped child.

The horizontal restraints 17 and 19 are selectively positioned in corresponding slots 3 in such a manner that a small child would have the lower waist belt 27 in one of the pair of lower slots 3 and the chest restraint 19 in a correspondingly appropriate upper pair of slots. A taller child obviously would have the pair of parallel belt restraints positioned farther apart with the chest restraint very close to the top. By use of the adjustable hook-loop fasteners, the chest and belt restraints can be adapted for each particular child and can come in varying sizes. Even with varying sizes, the hook and loop fastening means can be tightened to a comfortable point depending upon the amount of outer clothing the child is wearing. For example, it is not necessary to change the entire unit from summer to winter, and the child may remain in the same seat with the same harness both summer and winter.

It will be appreciated that the harness does not require any permanent connection to the seat or the vehicle, and the waist and chest restraints can easily be adjusted or replaced as the need arises.

With the hook and loop or pile type fastening means, the child can be easily and quickly removed from the seat and harness by merely peeling back one portion relative to the other. At the same time, with this type of fastener, the lapped portions will provide sufficient joining power to restrain the child in the seat. Obviously, the invention is not intended to be a substitute for seat belts, but is intended for retarded, handicapped or other children for maintaining them generally within the selected seats during normal travel. Other devices, such as seat belts, seat positioning, padding, and the like are provided by the school buses or school districts in conformance with local safety requirements.

While several embodiments of the invention have been described, it will be understood that it is capable of still further modifications and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A restraining harness for use on school buses, vans or other vehicles comprising:
   (a) a pair of straps,
   (b) said straps each having two ends and means for removably interconnecting said ends around the seat back for securely attaching the harness to a seat back,
   (c) a plurality of generally parallel, aligned loops formed on said straps,
   (d) a waist belt extending through a pair of said generally aligned loops and a chest belt extending through a pair of said generally aligned loops, and
   (e) means for adjustably connecting the ends of said belts around a person.

2. A harness as defined in claim 1 wherein said belt connecting means includes a plurality of minute hook members on one end for connecting to material on the other end.

3. A harness as defined in claim 1 wherein there are a plurality of loops of each strap for receiving said waist belt and a plurality of loops on each strap for receiving said chest belt.

4. A harness as defined in claim 1 including at least three pairs of loops for receiving said waist belt and at least five pairs of loops for receiving said chest belt.

5. A harness as defined in claim 1 including a pair of D-rings at one end of each of said straps.

6. A method for restraining a child in a school bus, van or other vehicle seat comprising:
   (a) providing a pair of straps each having two ends,
   (b) forming a plurality of parallel, aligned loops on each of said straps,
   (c) removably interconnecting said strap ends around a seat back in a substantially tight manner,
   (d) inserting a waist belt through a pair of generally aligned lower loops and inserting a chest belt through a pair of generally aligned upper loops,
   (e) placing a child on the seat between said straps and connecting said belts around the child to restrain the child on the seat and against the seat back.

7. The method of claim 6 including providing said belts, each having a pair of ends, with a plurality of minute hook members on one end and pile-like material on the other end, tightening the belt ends around the child and joining the two ends together by pressing the hook members onto the pile-like material.

* * * * *